United States Patent
Popp et al.

(10) Patent No.: US 6,635,041 B1
(45) Date of Patent: Oct. 21, 2003

(54) ABSORBENT GARMENT WITH ASYMMETRICAL LEG ELASTIC TENSION

(75) Inventors: Robert Lee Popp, Hortonville, WI (US); Robert Eugene Vogt, Neenah, WI (US); Joseph D. Coenen, Neenah, WI (US); Shawn A. Quereshi, Neenah, WI (US); Toan Thanh Le Minh, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/638,703

(22) Filed: Aug. 15, 2000

(51) Int. Cl.$^7$ .................................. A61F 13/15
(52) U.S. Cl. ........................ 604/385.25; 604/385.27; 604/385.24
(58) Field of Search .................. 604/385.21, 385.25, 604/385.26, 385.27

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,371,668 A | 3/1968 | Johnson | 128/290 |
| 3,468,748 A | 9/1969 | Bassett | 161/122 |
| 3,502,538 A | 3/1970 | Petersen | 161/150 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,061,063 A | 12/1977 | Brush | 83/55 |
| 4,300,562 A | 11/1981 | Pieniak | 128/287 |
| 4,300,967 A | 11/1981 | Sigl | 156/164 |
| 4,340,563 A | 7/1982 | Appel et al. | 264/518 |
| 4,371,417 A | 2/1983 | Frick et al. | 156/495 |
| 4,397,704 A | 8/1983 | Frick | 156/201 |
| 4,412,881 A | 11/1983 | Sigl | 156/164 |
| 4,432,823 A | 2/1984 | Moore | 156/164 |
| 4,486,192 A | 12/1984 | Sigl | 604/385 |
| 4,578,133 A | 3/1986 | Oshefsky et al. | 156/164 |
| 4,610,681 A | 9/1986 | Strohbeen et al. | 604/396 |
| 4,617,082 A | 10/1986 | Oshefsky et al. | 156/447 |
| 4,639,949 A | 2/1987 | Ales et al. | 2/400 |
| 4,641,381 A | 2/1987 | Heran et al. | 2/400 |
| 4,642,819 A | 2/1987 | Ales et al. | 2/400 |
| 4,646,362 A | 3/1987 | Heran et al. | 2/400 |
| 4,648,928 A | 3/1987 | Ales | 156/164 |
| 4,650,532 A | 3/1987 | Kloehn et al. | 156/204 |
| 4,663,220 A | 5/1987 | Wisneski et al. | 428/221 |
| 4,675,016 A | 6/1987 | Meuli et al. | 604/385 A |
| 4,687,477 A | 8/1987 | Suzuki et al. | 604/385 A |
| 4,692,163 A | * 9/1987 | Widlund et al. | 604/385 |
| 4,726,873 A | 2/1988 | Ales et al. | 156/495 |

(List continued on next page.)

FOREIGN PATENT DOCUMENTS

| | | | |
|---|---|---|---|
| CA | 1338133 | 3/1996 | 117/26 |
| EP | 0 217 032 | 4/1987 | D04H/13/00 |
| WO | 86/02530 | 5/1986 | |
| WO | 96/23477 | 8/1996 | |

*Primary Examiner*—Weilun Lo
*Assistant Examiner*—Jacqueline F. Stephens
(74) *Attorney, Agent, or Firm*—Pauley Petersen & Erickson

(57) ABSTRACT

A pant-like absorbent garment adapted to the non-symmetrical nature and leakage demands of the anatomy of the human body has asymmetrical pressure around the leg openings with respect to the wearer's anterior and posterior sides. Elastic members are bonded about the leg openings with either higher tension on the posterior side and lower tension on the anterior side or higher tension on the anterior side and lower tension on the posterior side, depending on the intended wearer's level of activity. The resulting garments have optimized comfort, fit and containment about the leg openings.

20 Claims, 7 Drawing Sheets

U.S. PATENT DOCUMENTS

| | | | |
|---|---|---|---|
| 4,743,241 A | 5/1988 | Igaue et al. | 604/385 A |
| 4,747,846 A | 5/1988 | Boland et al. | 604/38 A |
| 4,762,582 A | 8/1988 | de Jonckheere | |
| 4,786,346 A | 11/1988 | Ales et al. | 156/160 |
| 4,863,542 A | 9/1989 | Oshefsky et al. | 156/160 |
| 4,915,767 A | 4/1990 | Rajala et al. | 156/440 |
| 4,917,746 A | 4/1990 | Kons et al. | 156/164 |
| 4,940,464 A | 7/1990 | Van Gompel et al. | 604/396 |
| 4,943,340 A | 7/1990 | Ujimoto et al. | 156/496 |
| 4,946,539 A | 8/1990 | Ales et al. | 156/495 |
| 5,046,272 A | 9/1991 | Vogt et al. | 38/143 |
| 5,055,103 A | 10/1991 | Nomura et al. | 604/385.2 |
| 5,092,861 A | 3/1992 | Nomura et al. | 604/385.2 |
| 5,104,116 A | 4/1992 | Pohjola | 271/185 |
| 5,143,679 A | 9/1992 | Weber et al. | 264/288.8 |
| 5,147,487 A | 9/1992 | Nomura et al. | 156/164 |
| 5,156,793 A | 10/1992 | Buell et al. | 264/288.8 |
| 5,167,897 A | 12/1992 | Weber et al. | 264/288.8 |
| 5,171,388 A | 12/1992 | Hoffman et al. | 156/164 |
| 5,180,534 A | 1/1993 | Thomas et al. | 264/145 |
| 5,213,645 A | 5/1993 | Nomura et al. | 156/164 |
| 5,224,405 A | 7/1993 | Pohjola | 83/24 |
| 5,226,992 A | 7/1993 | Morman | 156/62.4 |
| 5,230,851 A | 7/1993 | Thomas | 264/145 |
| 5,259,902 A | 11/1993 | Muckenfuhs | 156/164 |
| 5,275,676 A | 1/1994 | Rooyakkers et al. | 156/164 |
| 5,318,741 A | 6/1994 | Thomas | 264/519 |
| 5,326,415 A | 7/1994 | Thomas et al. | 156/244.11 |
| 5,334,152 A | 8/1994 | Nomura et al. | 604/385.2 |
| 5,342,341 A | 8/1994 | Igaue et al. | 604/385.2 |
| 5,354,400 A | 10/1994 | Lavash et al. | 156/227 |
| 5,385,706 A | 1/1995 | Thomas | 264/519 |
| 5,389,173 A | 2/1995 | Merkatoris et al. | 156/164 |
| 5,393,360 A | 2/1995 | Bridges et al. | 156/73.3 |
| 5,407,507 A | 4/1995 | Ball | 156/163 |
| 5,413,654 A | 5/1995 | Igaue et al. | 156/161 |
| 5,454,803 A | 10/1995 | Sageser et al. | 604/385.2 |
| 5,500,075 A | 3/1996 | Herrmann | 156/494 |
| 5,503,919 A | 4/1996 | Litchholt et al. | 428/286 |
| 5,509,985 A | 4/1996 | Kock | 156/160 |
| 5,516,392 A | 5/1996 | Bridges et al. | 156/160 |
| 5,517,737 A | 5/1996 | Viltro et al. | 26/88 |
| 5,518,566 A | 5/1996 | Bridges et al. | 156/161 |
| 5,525,175 A | 6/1996 | Blenke et al. | 156/161 |
| 5,540,672 A | 7/1996 | Roessler et al. | |
| 5,547,531 A | 8/1996 | Allen et al. | 156/164 |
| 5,622,578 A | 4/1997 | Thomas | 156/66 |
| 5,662,636 A | 9/1997 | Benjamin et al. | 604/385.2 |
| 5,683,531 A * | 11/1997 | Roessler et al. | 156/164 |
| 5,704,930 A | 1/1998 | Lavash et al. | 604/385.2 |
| 5,723,087 A | 3/1998 | Chappell et al. | 264/284 |
| 5,733,401 A | 3/1998 | Linman et al. | 156/160 |
| 5,745,922 A | 5/1998 | Rajala et al. | 2/243.1 |
| 5,749,865 A | 5/1998 | Yamamoto et al. | 604/385.2 |
| 5,749,989 A | 5/1998 | Linman et al. | 156/160 |
| 5,772,825 A | 6/1998 | Schmitz | 156/164 |
| 5,776,121 A | 7/1998 | Roe et al. | 604/385.1 |
| 5,779,689 A | 7/1998 | Pfeifer et al. | |
| 5,916,206 A * | 6/1999 | Otsubo et al. | 604/385.2 |

* cited by examiner

ABSORBENT GARMENT WITH ASYMMETRICAL LEG ELASTIC TENSION

FIELD OF THE INVENTION

This invention is directed to pant-like, personal care absorbent products having asymmetrical tension around the leg openings with respect to an imaginary dividing plane between a wearer's anterior and posterior sides. More particularly, elastic members around the leg openings have varying tension to adapt to the non-symmetrical nature and leakage demands of the anatomy of the human body for ideal gasketing.

BACKGROUND OF THE INVENTION

Pant-like absorbent garments, such as adult incontinence wear as well as infant and children's diapers, swim wear and training pants, typically include a pair of leg openings having an elastic portion around each leg opening. The elastic portions are intended to fit snugly around a wearer's legs to prevent leakage from the garment. However, more pressure is required in certain areas around the leg, such as in the crotch area, than in other areas around the leg, such as in the dwell area away from the crotch in order to increase the gasketing effect. Furthermore, pressure variation requirements differ depending on the wearer's activities.

For example, for infants, the crotch area is typically the area around the leg openings most susceptible to leakage, while leg opening areas away from the crotch area are typically less susceptible to leakage. When uniform pressure is applied around the leg openings, if the pressure is too great, leakage in the susceptible areas is prevented, but the high pressure creates discomfort in the areas less susceptible to leakage. Likewise, if the pressure is uniform yet too loose, it is likely that not enough pressure is exerted in the areas more susceptible to leakage to prevent leakage in those areas.

In overnight use when a child sleeps on its stomach, the front areas of the legs are more susceptible to leakage than the back areas of the legs. Furthermore, in the sleeping position when the wearer's legs are extended, greater comfort is desired in the back areas of the legs.

Active children have different gasketing and comfort requirements than infants or sleeping children. For example, forward movement of the legs is hindered when too much pressure is present in the front areas of the legs. Likewise, when the legs move forward, the back areas of the legs are more susceptible to leakage.

There is a need or desire for leg elastics for absorbent garments that have customized pressure and gasketing around the leg openings to adapt to the nonsymmetrical nature and leakage demands of the anatomy of the human body.

SUMMARY OF THE INVENTION

It has been found that variation in tension among elastic members is a factor that can be optimized to provide enhanced comfort, fit and containment about the leg openings by providing optimized pressure and gasketing. More particularly, such optimization is achieved with asymmetrical tension in the elastic members around the leg openings with respect to an imaginary dividing plane between a wearer's anterior and posterior sides.

The present invention is directed to customized pressure around the leg openings of pant-like absorbent garments, such as diapers and training pants. The resulting garment has asymmetrical pressure around the leg openings with respect to a wearer's anterior and posterior sides. Such pressure variation is customized according to the wearer's level of activity to provide greater leakage protection while maintaining maximum comfort.

The invention is achieved by varying the tension in the elastic members as the elastic members are applied to the leg openings of the absorbent garment. Alternatively, elastic materials having different levels of tension can be used, or the density of ultrasonic bonds used to attach the elastic members to the absorbent garment can be varied. Any of these methods can be used alone or in combination to achieve the product of the invention.

The variable tension is adapted to the non-symmetrical nature and leakage demands of the anatomy of the human body for increased comfort as well as a gasket-like fit about the wearer's legs. As a result, the tension profile of the leg elastics in the resulting absorbent garment is asymmetrical with respect to the front and back of the wearer's body. Furthermore, greater gasketing (better leakage prevention) is provided in areas where leakage is more likely to occur and lower tension is provided for greater comfort in areas where leakage is less likely to occur.

With the foregoing in mind, it is a feature and advantage of the invention to provide customized pressure by varying the tension of the elastic members around the leg openings of an absorbent garment resulting in optimized performance of the leg elastic in terms of comfort, fit and containment.

DEFINITIONS

Figure 1:
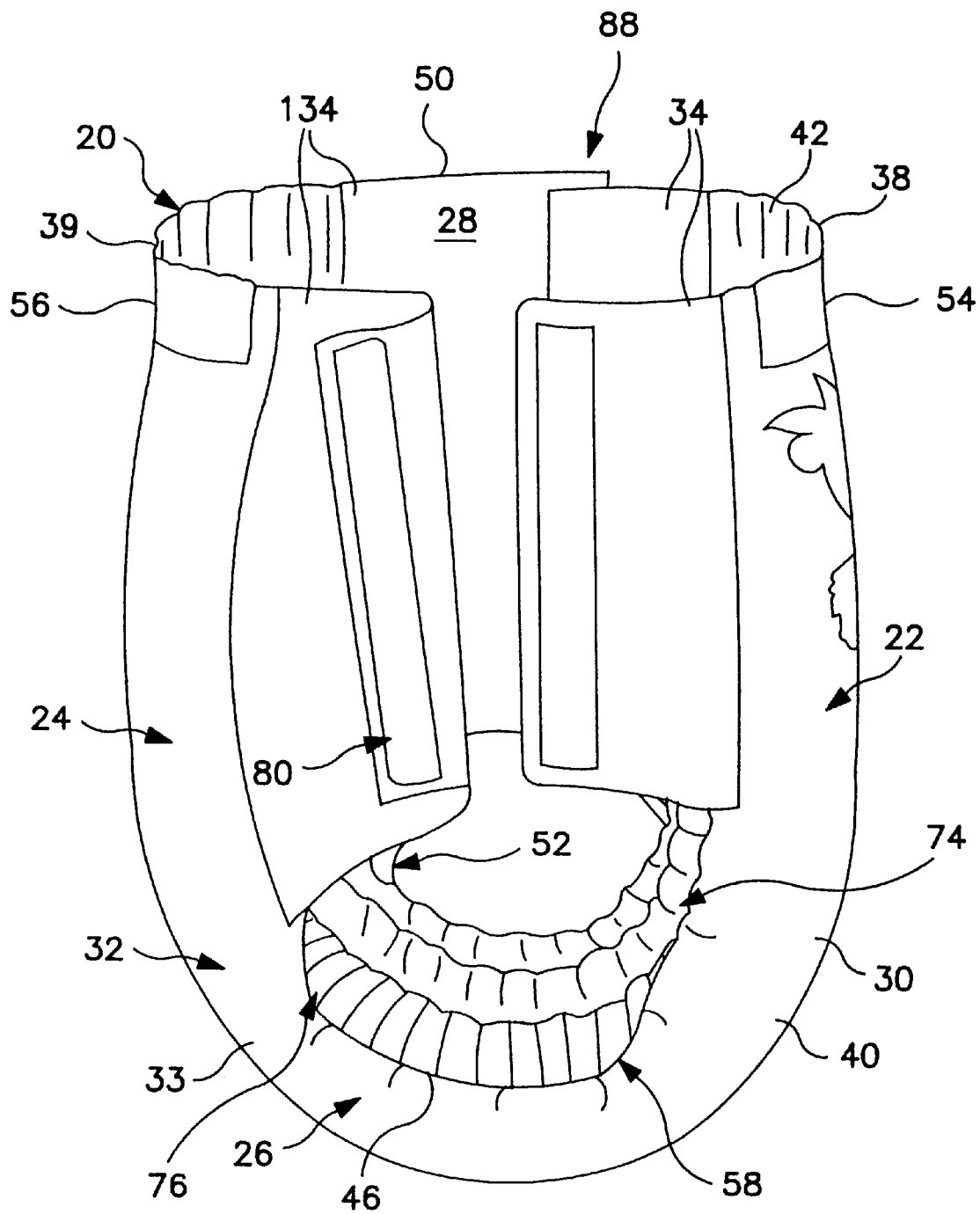
FIG. 1 is a side perspective view of an absorbent garment.

Within the context of this specification, each term or phrase below will include the following meaning or meanings.

"Anterior" refers to a location on the front, or ventral surface, of a wearer's body.

"Asymmetrical" refers to lack of exact correspondence of form and constituent configuration on opposite sides of a dividing line or plane.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid. The term also includes film-like materials that exist as open-celled foams.

"Force" includes a physical influence exerted by one body on another which produces acceleration of bodies that are free to move and deformation or separation of bodies that are not free to move.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Inward" and "outward" refer to positions relative to the center of an absorbent article, and particularly transversely and/or longitudinally closer to or away from the longitudinal and transverse center of the absorbent article.

"Layer" when used in the singular can have the dual meaning of a single element or a plurality of elements.

"Leg elastic" includes elastic bands, strands, ribbons, filaments, filament bunches and the like, which are adjacent to a garment opening that receives a wearer's leg.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid-permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 3:
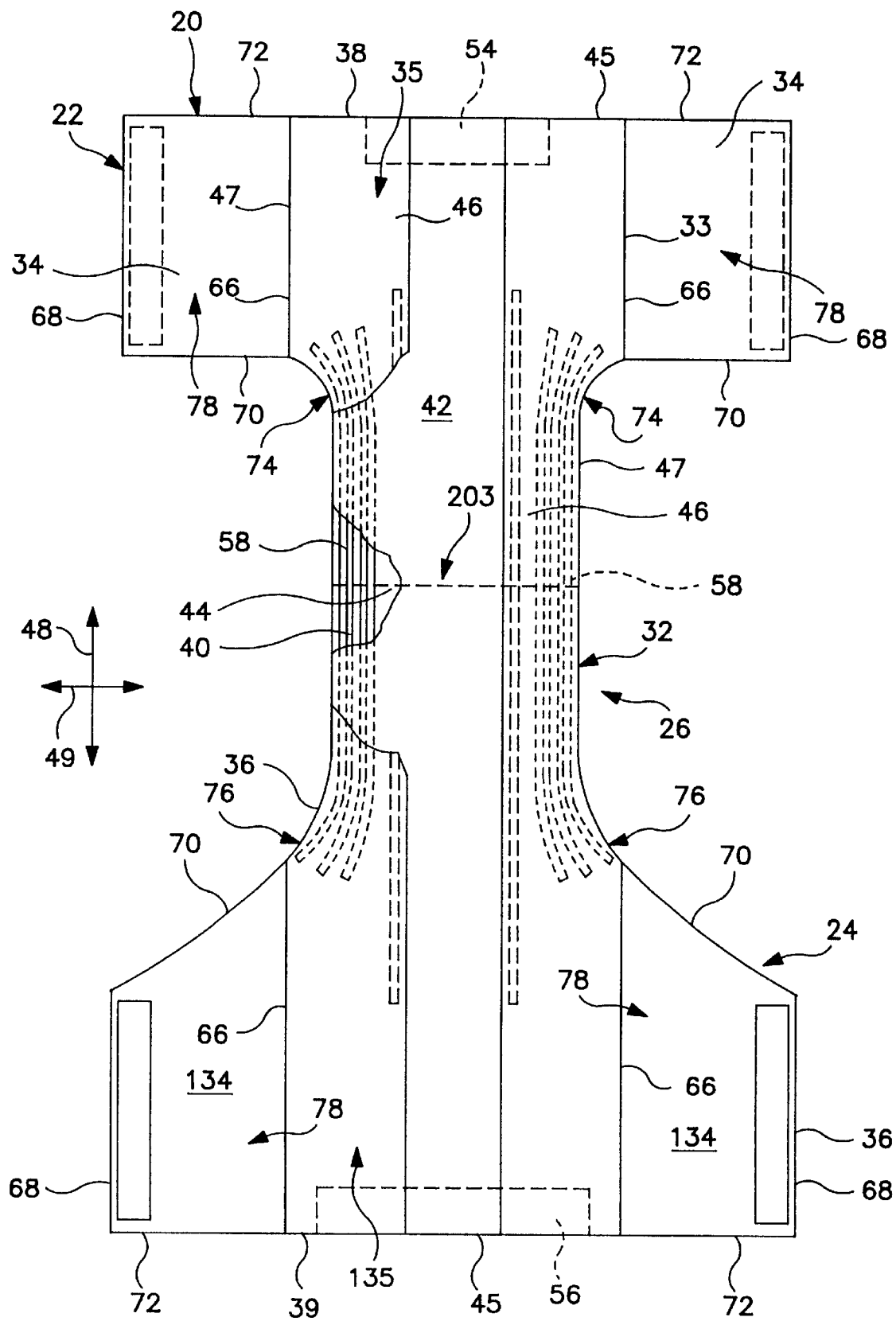
FIG. 3 is a plan view of the absorbent garment of FIGS. 1 and 2 in a partially disassembled, stretched flat state, and showing the surface of the article that faces the wearer when the article is worn, and with portions cut away to show the underlying features.

"Longitudinal" and "transverse" have their customary meaning, as indicated by the longitudinal and transverse axes depicted in FIG. 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a nonelastic member to another element, means that the member and element can be attached in any suitable manner that permits or allows them to perform the intended or described function of the composite. The joining, attaching, connecting or the like can be either directly, such as joining either member directly to an element, or can be indirectly by means of another member disposed between the first member and the first element, or can be such that the first member is mechanically trapped by adjacent bond points in the first element such that the first member causes the composite to exhibit characteristics of the first member.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as, for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Posterior" refers to a location on the back, or dorsal surface, of a wearer's body.

"Pressure" refers to a force per unit area as applied to the wearer's skin to provide gasketing.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, by at least 50% (to 150% of its initial (unstretched) length) in at least one direction, suitably by at least 100% (to 200% of its initial length), desirably by at least 150% (to at least 250% of its initial length).

"Surface" includes any layer, film, woven, nonwoven, laminate, composite, or the like, whether pervious or impervious to air, gas, and/or liquids.

"Tension" includes a uniaxial force tending to cause the extension of a body or the balancing force within that body resisting the extension.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a pant-like absorbent garment having asymmetrical tension to achieve asymmetrical pressure around a pair of leg openings. The tension is asymmetrical with respect to an imaginary dividing plane between a wearer's anterior and posterior sides. More particularly, greater pressure on either the anterior or posterior side of the garment and lower pressure on the opposite side creates optimum comfort, fit and containment about the leg openings in accordance with the wearer's level of activity.

The principles of the present invention can be incorporated into any suitable disposable absorbent article. Examples of such suitable articles include diapers, training pants, feminine hygiene products, incontinence products, other personal care or health care garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Figure 2:
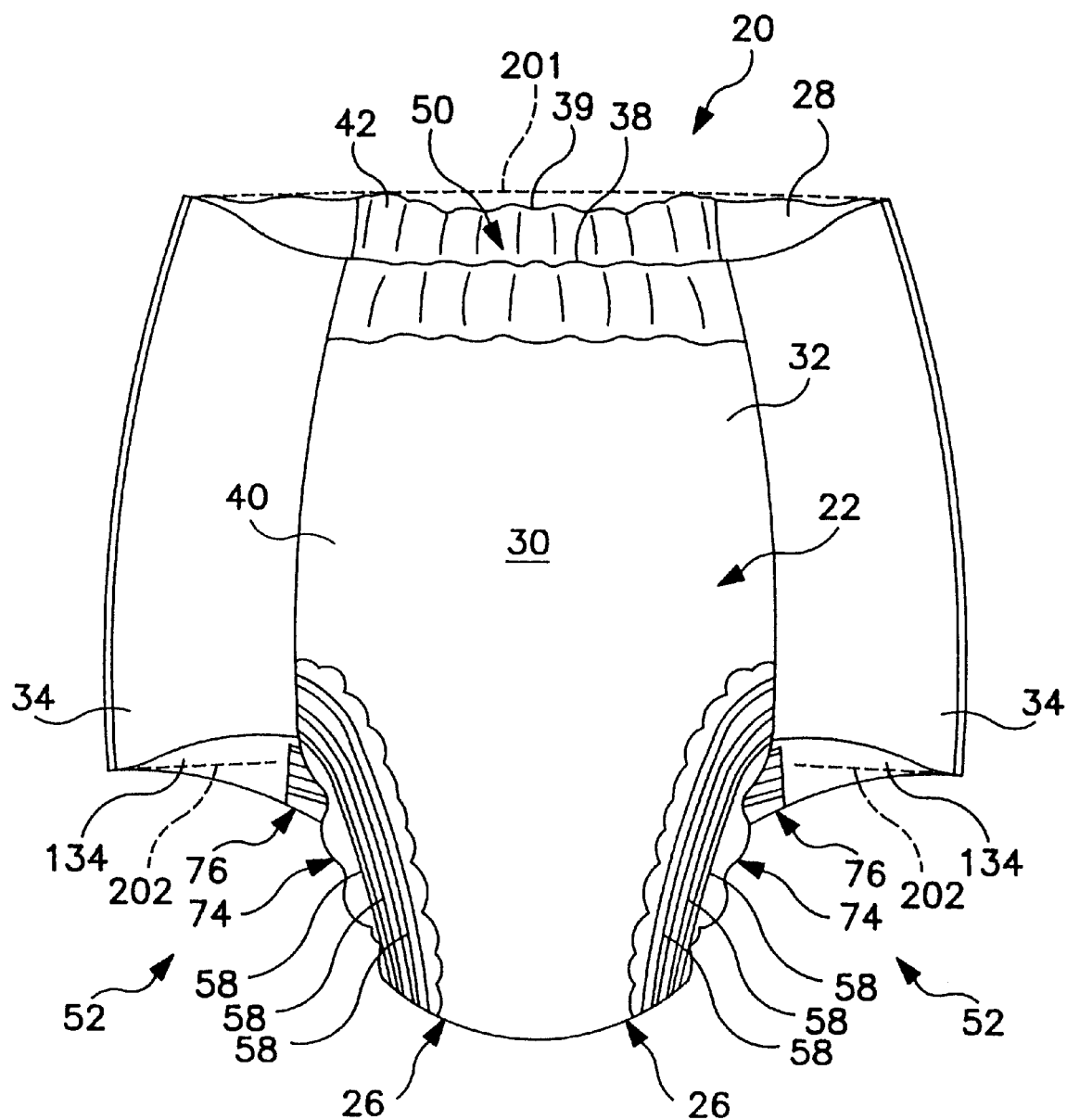
FIG. 2 is a front perspective view of an absorbent garment.

Referring to FIGS. 1 and 2, a disposable absorbent article, such as a training pant 20, is illustrated in a partially fastened condition and in a fastened condition, respectively. The training pant 20 includes an absorbent chassis 32 and leg elastic members 58. The absorbent chassis 32 defines an anterior side 22, a posterior side 24, a crotch region 26 interconnecting the anterior and posterior sides, an inner surface 28 which is configured to contact the wearer, and an outer surface 30 opposite the inner surface which is configured to contact the wearer's clothing. With additional reference to FIG. 3, the absorbent chassis 32 also defines a pair of transversely opposed side edges 36 and a pair of longitudinally opposed waist edges, which are designated front waist edge 38 and back waist edge 39. The anterior side 22 is contiguous with the front waist edge 38, and the posterior side 24 is contiguous with the back waist edge 39. The imaginary dividing plane between the anterior and posterior sides 22, 24 extends from the center of the left side of the garment to the center of the right side of the garment, as shown by the dotted lines 201 and 202 in FIG. 2, thereby dividing the garment in half, as shown by the dotted line 203 in FIG. 3. The asymmetrical characteristics of the leg elastics (described below) are determined with respect to a plane which includes both lines 201 and 202 and bisects the garment along line 203.

The illustrated absorbent chassis 32 includes a somewhat rectangular composite structure 33, a pair of transversely opposed front side panels 34, and a pair of transversely opposed back side panels 134. The composite structure 33 and side panels 34 and 134 may be integrally formed or may include two or more separate elements, as shown in FIGS. 1–3. The illustrated composite structure 33 includes an outer cover 40, a bodyside liner 42 which is connected to the outer cover in a superposed relation, an absorbent assembly 44 which is located between the outer cover 40 and the bodyside liner 42, and a pair of containment flaps 46. The rectangular composite structure 33 has opposite linear end edges 45 that form portions of the front and back waist edges 38 and 39, and opposite linear, or curvilinear, side edges 47 that form portions of the side edges 36 of the absorbent chassis 32. Leg openings 52 (FIGS. 1 and 2) are generally defined by portions of the transversely opposed side edges 36 in the crotch region 26. For reference, arrows 48 and 49 depicting the orientation of the longitudinal axis and the transverse axis, respectively, of the training pant 20 are illustrated in FIG. 3.

The leg elastic members 58 are operatively joined to the outer cover 40 and/or bodyside liner 42 along the opposite edges 36 and positioned in the crotch region 26 of the training pant 20 to prevent leakage. When the side panels 34, 134 are present, the leg elastic members 58 typically surround the portions of the leg openings 52 not covered by the side panels 34, 134, but still encompass a portion of the anterior side 22, the crotch region 26, and a portion of the posterior side 24. As used herein, the term "crotch region" refers to the area of the garment 20 located between a wearer's legs. As mentioned, the dashed line 203 in FIG. 3 represents a boundary between the anterior side 22 and the posterior side 24. The term "front area" refers to areas of the garment 20 located in front of a wearer's legs. Similarly, the term "back area" refers to areas of the garment 20 located in back of a wearer's legs. A front area 74 of the leg openings 52 is located on the anterior side 22. Similarly, a back area 76 of the leg openings 52 is located on the posterior side 24. The areas of the garment 20 located in front of a wearer's legs (i.e., the anterior side 22, including the front area 74 of the leg openings 52), behind the wearer's legs (i.e., the posterior side, including the back area 76 of the leg openings 52), and on outer portions of the wearer's legs are considered to be away from, or outside of, the crotch region 26.

Terms such as "tension," "greater tension" and "lower tension" may be defined in terms of the amount of retractive force experienced in a selected region of the elastic member, compared to the average retractive force experienced in all regions covered by the elastic member, when the elastic member is stretched to 125% of an initial length, as may be the case when the garment is worn by a wearer. Generally, a region is defined as having "higher tension" if the retractive force exhibited by the elastic member in that region is at least 10% greater, preferably at least 20% greater than the average retractive force in all regions covered by the elastic member (for example, the average retractive force around a leg or waist opening). Generally, a region is defined as having "lower tension" if the retractive force exhibited by the elastic member in that region is at least 10% less, preferably at least 20% less than the average retractive force in all regions covered by the elastic member. Generally, a region is defined as having "medium tension" or "intermediate tension" if the retractive force exhibited by the elastic member in that region is more than 90% and less than 110% of the average retractive force in all regions covered by the elastic member. These comparative terms for tension apply to garments in a relaxed state. More particularly, when the garment is in a relaxed state, tension levels in the elastic members may vary, depending on the manner in which they are bonded to the garment. For example, when an elastic member is stretched as it is bonded to the garment, a greater amount of stretch during the bonding process yields greater tension in the elastic member subsequent to the bonding process.

Normally, high gasketing pressure is desirable in the crotch region 26 of the absorbent garment 20 to provide leakage protection, while lower pressure is often desirable in the front area 74 of the leg openings 52 and/or the back area 76 of the leg openings 52 away from the crotch area 26 for greater comfort. However, different activities have different pressure demands, resulting in an optimum pressure profile that is asymmetrical with respect to an imaginary dividing plane between a wearer's anterior and posterior sides. For example, when a wearer is sleeping on his or her stomach, higher pressure on the anterior side 22 is appropriate to combat higher susceptibility to leakage in this area while lower pressure on the posterior side 24 is appropriate to provide greater comfort in areas less susceptible to leakage. Therefore, an absorbent garment 20 optimized for use while the wearer is sleeping on his or her stomach preferably has greater tension in the leg elastic members 58 bonded to the front area 74 of the leg openings 52 for greater gasketing pressure and less tension in the leg elastic members 58 bonded to the back area 76 of the leg openings 52 for greater comfort. Furthermore, tension in the leg elastic members 58 bonded to the crotch region 26 can be intermediate or else roughly equal to the level of tension on either the anterior side 22 or the posterior side 24.

Active children have different gasketing and comfort requirements than infants or sleeping children. Having reduced tension on the anterior side 22 provides lower pressure concentration on the front of the wearer's leg, thereby allowing for forward movement of the leg. Greater tension on the posterior side 24 provides greater gasketing pressure when the leg moves forward. Therefore, an absorbent garment 20 optimized for use by an active wearer preferably has lower tension in the leg elastic members 58 bonded to the front area 74 of the leg openings 52 for easier mobility, and greater tension in the leg elastic members 58 bonded to the back area 76 of the leg openings 52 for greater gasketing pressure. Furthermore, tension in the leg elastic members 58 bonded to the crotch region 26 can be intermediate or else roughly equal to the level of tension on either the anterior side 22 or the posterior side 24.

Several methods are available for achieving variations in leg elastic tension. For example, variations in leg elastic tension can be achieved by directly varying the tension in the leg elastic members 58 during application, either by feeding the leg elastic members 58 at different rates or by stretching the leg elastic members 58 to varying degrees along the lengths of the leg elastic members 58. One such method of varying the tension in the elastic members is disclosed in U.S. Pat. No. 4,371,417 issued Feb. 1, 1983, to Frick et al., herein incorporated by reference. Other methods for varying tension in the leg elastic members 58 are carried out using apparatus 3 shown in FIGS. 4–9. Furthermore, tension variation can be achieved using elastic materials having varying elastic properties. Such materials can be applied with constant levels of elongation and still result in variable tension around the leg openings 52. Variations in leg elastic tension can also be achieved by varying density of ultrasonic bonds, i.e. the sonic bond pattern, used to attach the leg elastic members 58 to the absorbent garment 20. Any of these methods can be used alone or in combination to achieve the product of the invention.

Figure 4:
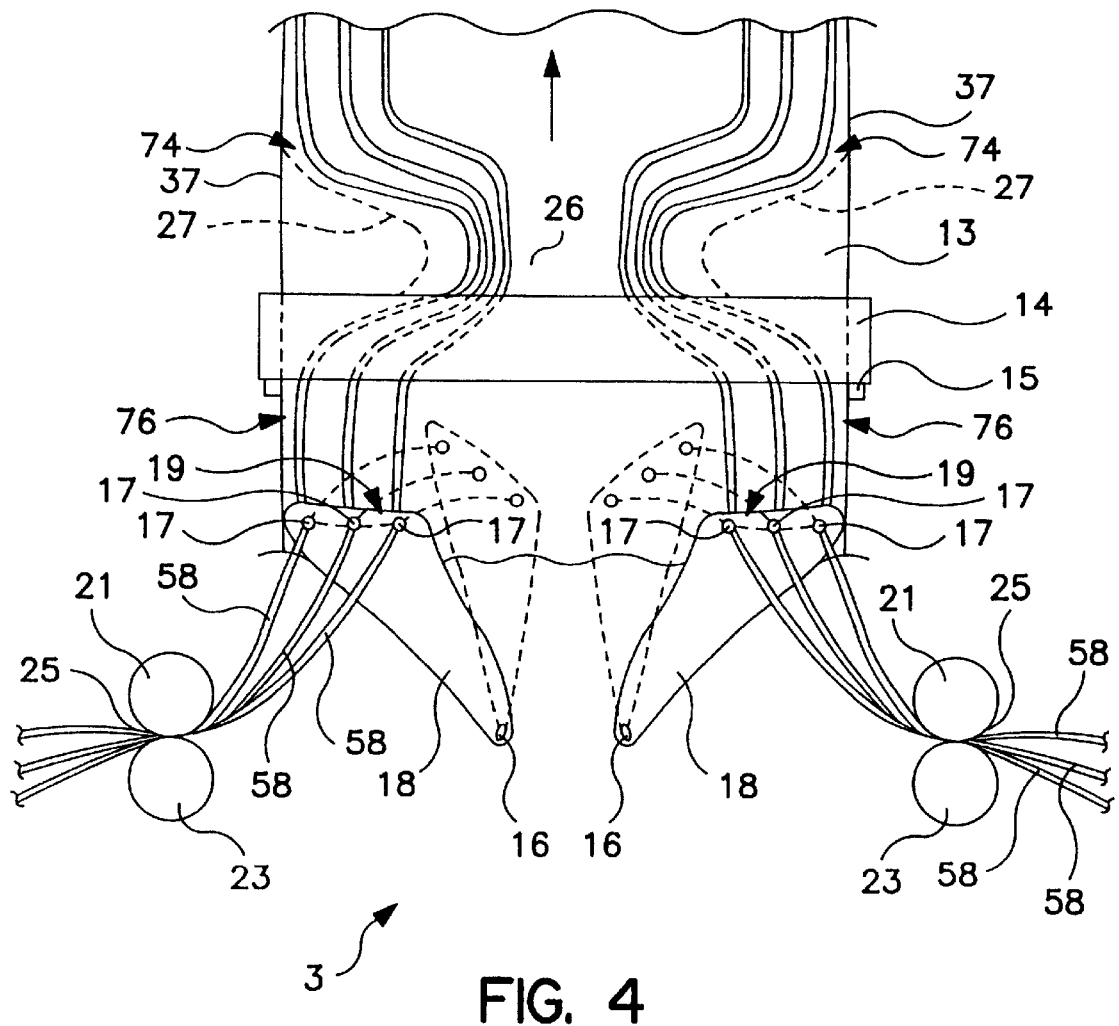
FIG. 4 is a top plan view of one type of apparatus used for applying leg elastics to an absorbent garment to produce one embodiment of the invention.
Figure 5:
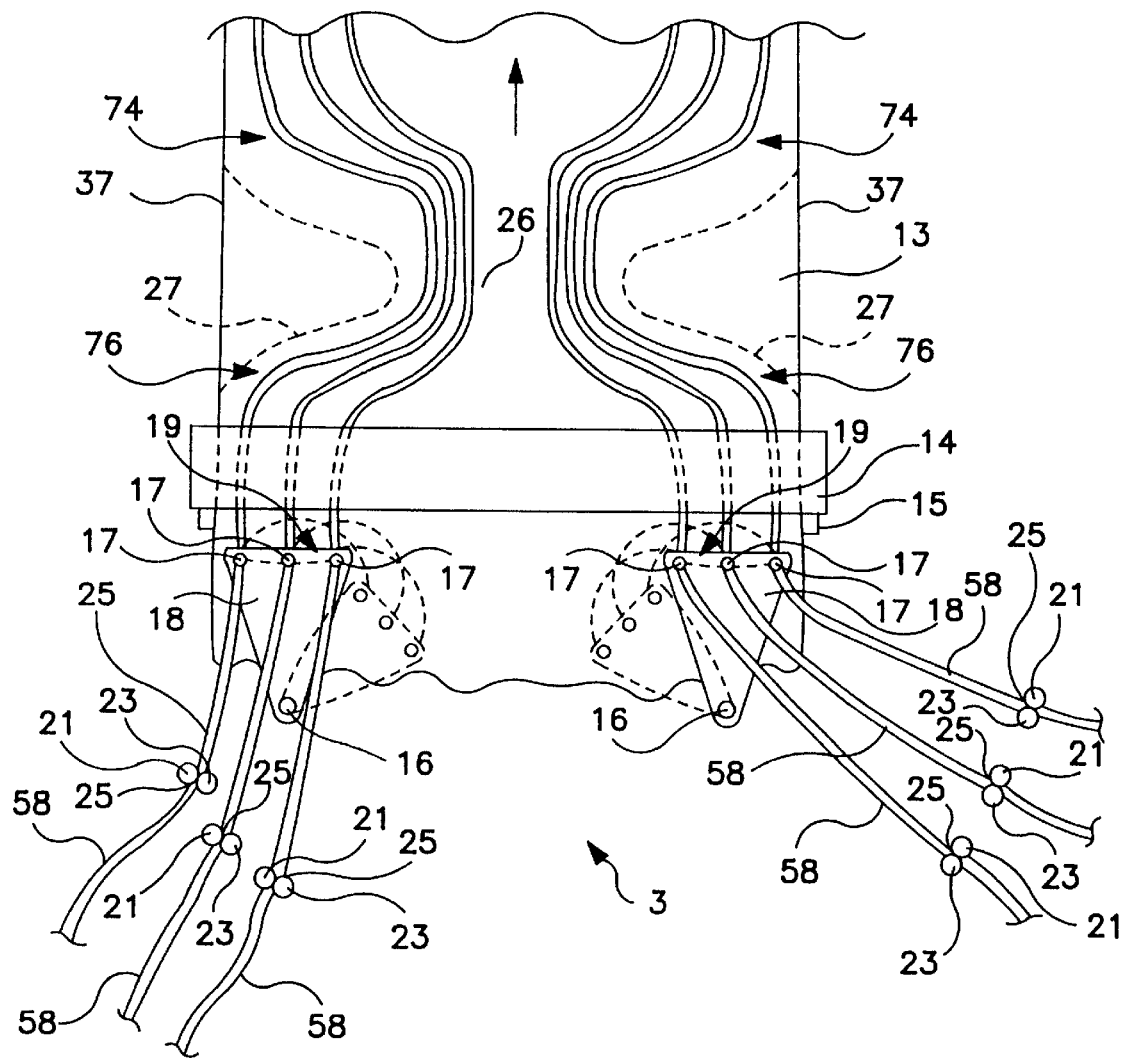
FIG. 5 is a top plan view of a second type of apparatus used for applying leg elastics to an absorbent garment to produce one embodiment of the invention.
Figure 6:
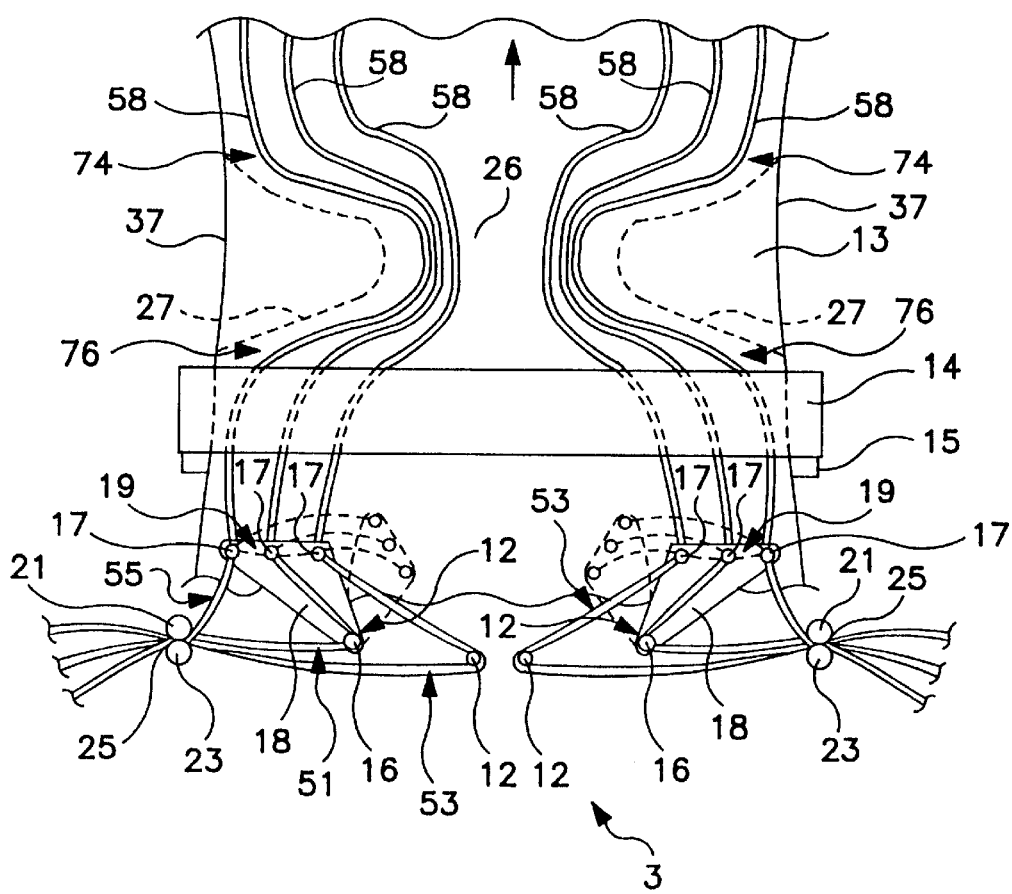
FIG. 6 is a top plan view of a third type of apparatus used for applying leg elastics to an absorbent garment to produce one embodiment of the invention.
Figure 8:
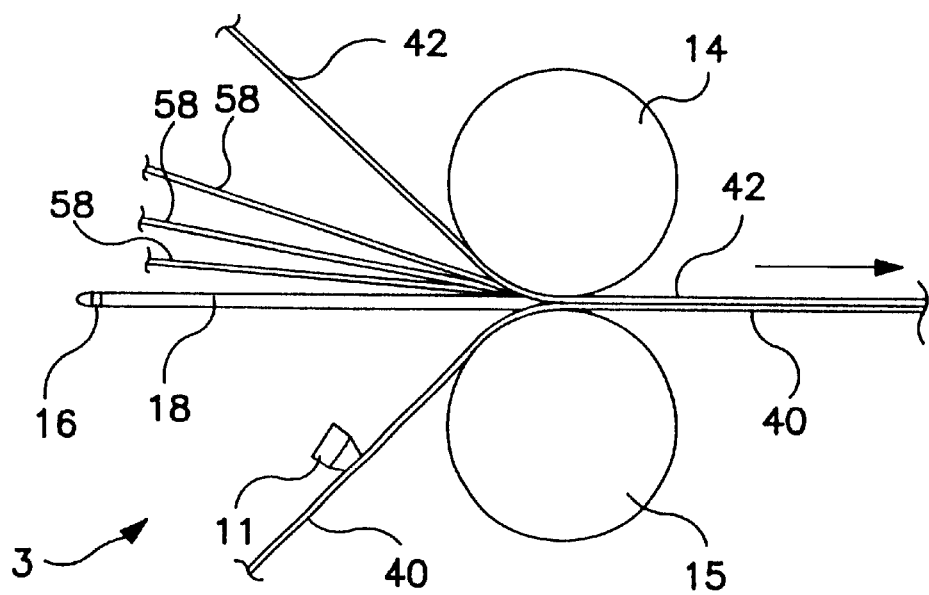
FIG. 8 is a side view of any of FIGS. 4–6.
Figure 9:
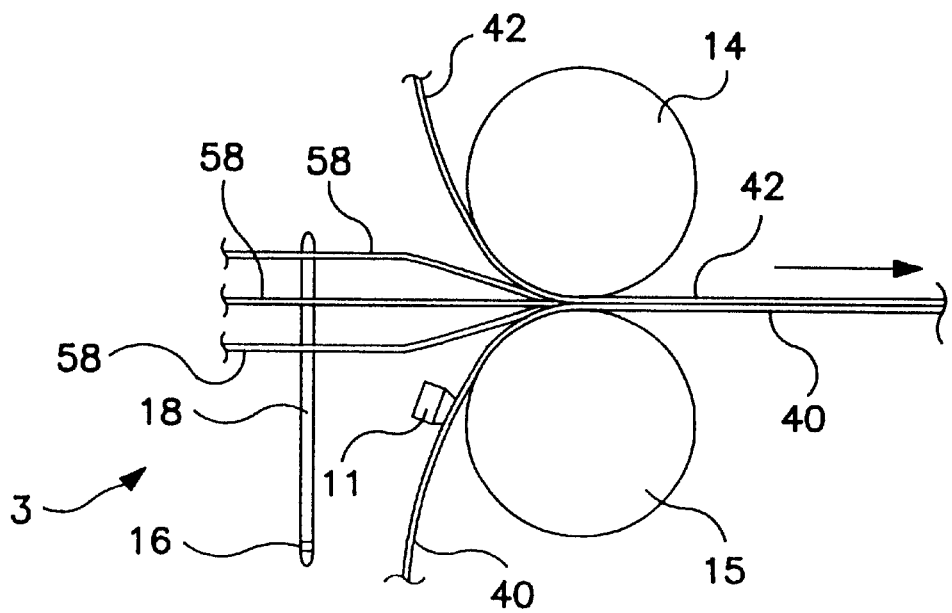
FIG. 9 is an alternative side view of any of FIGS. 4–6.

One example of apparatus for producing the invention is shown generally in FIG. 4. This apparatus 3 is used to apply the leg elastic members 58 to a substrate 13, namely part of the chassis 32 of the absorbent garment 20, with variable tension in the members 58. In doing so, a pivot arm 18 pivots in a plane substantially parallel, as shown in FIG. 8, or perpendicular, as shown in FIG. 9, to the substrate 13 (e.g. the outer cover 40) as the substrate 13 is fed through a pair of nip rolls 14 and 15 in a machine direction (indicated by the arrows in FIGS. 4–9). As used herein, the term "machine direction" means the length of a fabric in the direction in which it is produced. Alternatively, the pivot arms 18 can pivot in a plane at an angle between parallel and perpendicular to the substrate 13. The pivot arm 18 guides the leg elastic members 58 from a strategically placed feed nip 25 (including nip rolls 21 and 23), through elastic guide openings 17 on the pivot arm 18, to the substrate 13 to which the members 58 are ultimately bonded. The elastic guide openings 17 are preferably spaced at different radii from a pivot point 16 on the pivot arm 18. The pivot arm 18 pivots from side to side thereby varying the tension in the leg elastic members 58 as well as aligning the leg elastic members 58 in appropriate placement on the substrate 13. This apparatus 3 can provide customized higher tension anywhere about the leg opening 52 for higher gasketing pressure, and lower tension over any area about the leg opening 52 for better comfort. Placement of the leg elastic members 58 about the leg openings 52 can be customized in any shape on the product 20 which would offer an ideal fit all the way around the wearer's leg. For example, the leg elastic members 58 can be curved inward in the crotch region 26, as shown in FIGS. 4–6. Furthermore, the position of rolls 21 and 23 can be varied, thereby varying the location of high and low tension areas on the product 20.

Each elastic guide opening 17 on the pivot arm 18 preferably guides an individual leg elastic member 58. As the pivot arm 18 moves the elastic guide openings 17 away from the feed nip 25, tension in the leg elastic members 58 increases due to increased elongation while the pivot arm 18 is moving. As the substrate 13 travels in the machine direction prior to passing through the pair of nip rolls 14 and 15, the leg elastic members 58 are bonded, also in the machine direction, along, near, or between outer edges 37 of the substrate 13. Leg contours 27 can be pre-cut along the outer edges 37 of the substrate 13 or may be cut along the contour of the leg elastic members 58 subsequent to the bonding process. As the elastic guide openings 17 guide the leg elastic members 58 toward the crotch region 26, the elastic guide openings 17 are moved away from the feed nip 25, thereby causing increased tension in the leg elastic members 58 in the crotch region 26 as the leg elastic members 58 are bonded to the substrate 13. The regions in which the leg elastic members 58 are bonded to the substrate 13 ultimately end up forming the leg openings 52 (FIGS. 1 and 2).

Another example of apparatus for producing the invention is shown generally in FIG. 5. Like the apparatus 3 in FIG. 4, this apparatus 3 includes a pair of pivot arms 18 having elastic guide openings 17, but instead of just one strategically placed feed nip 25 for each pivot arm 18, this apparatus includes a separate, strategically placed feed nip 25 (including nip rolls 21 and 23) for each leg elastic member 58. Another difference between FIGS. 4 and 5 is the fact that the guide openings 17 are at different radii from the pivot point 16 in FIG. 4 and are at roughly the same radial distance from the pivot point 16 in FIG. 5. By having separate feed nips 25 for each leg elastic member 58, the tension profile of each leg elastic member 58 can be different. As the pivot arm 18 moves the elastic guide openings 17 away from each of the feed nips 25, tension in the respective leg elastic members 58 increases. The ratio of the leg elastic member path length between the feed nip 25 and the corresponding elastic guide opening 17 at any given pivot arm position determines the amount of elastic tension in the leg elastic member 58. When the path is shorter, the respective member 58 exhibits less stretching and less tension. When the path is longer, the member 58 exhibits greater stretching and tension. The respective speeds of the feed nips 25 and the nip rolls 14, 15 also affects elastic tension of the members 58. The feed nips 25 can be driven at the same constant speed for uniform tension profiles among the leg elastic members 58, or at different speeds for varying tension profiles. Like the apparatus in FIG. 4, as the elastic guide openings 17 guide the leg elastic members 58 toward the crotch region 26, the elastic guide openings 17 are moved away from the feed nips 25, thereby causing increased tension in the leg elastic members 58 in the crotch region 26 as the leg elastic members 58 are bonded to the substrate 13.

Yet another example of apparatus for carrying out the invention is shown generally in FIG. 6. Like the apparatuses in FIGS. 4 and 5, this apparatus 3 includes a pair of pivot arms 18 having elastic guide openings 17 and at least one strategically placed feed nip 25 for each pivot arm 18. However, this apparatus 3 also features at least one strategically placed idler roll 12 to change the path length, and the stretching amount, of individual leg elastic members 58. By locating the idler rolls 12 in various positions, the tension profile of each leg elastic member 58 can be different. For example, with an idler roll 12 on a pivot point 16 of the pivot arm 18, as shown in a position 51 in FIG. 6, the tension in the corresponding leg elastic member 58 will be constant. With an idler roll 12 closer to the crotch region 26, as shown in a position 53 in FIG. 6, the tension will be higher in the corresponding leg elastic member 58 in the area away from the crotch region 26. In contrast, when the leg elastic member 58 is not wrapped about an idler roll 12, and the feed nip 25 is located close to the pivot arm 18 when the pivot arm 18 is pivoted away from the crotch region 26, as shown in a position 55 in FIG. 6, the tension in the leg elastic member 58 is high in the crotch region 26.

Figure 7:
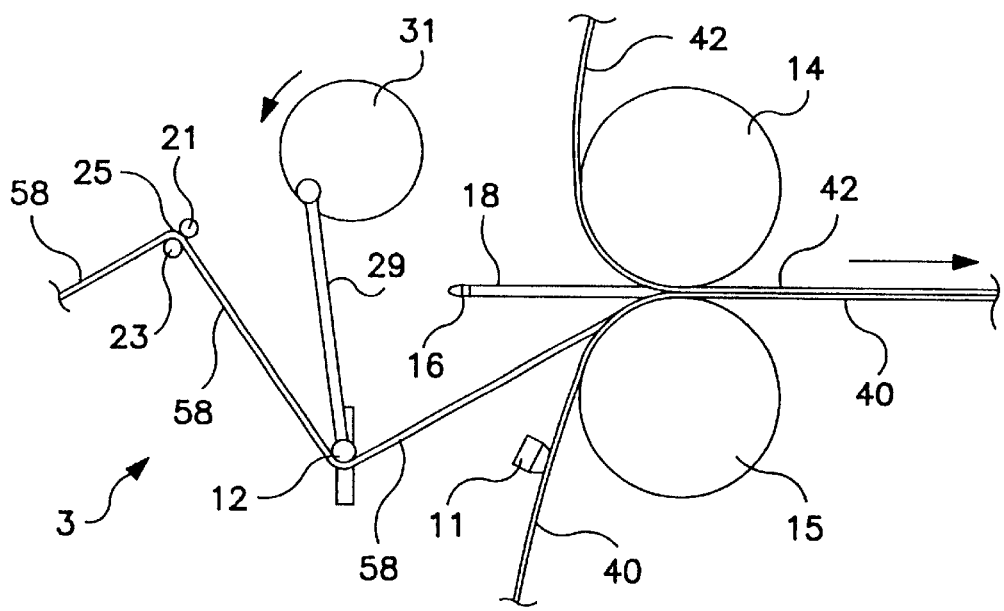
FIG. 7 is a side view of apparatus used for varying elongation of elastic members.

Another arrangement for varying tension along the leg elastic members 58 is shown in FIG. 7. The arrangement includes an idler roll 12 on a shaft 29 connected to a rotating wheel 31. The elongation, and resulting tension, of the leg elastic member 58 is varied based on the distance from the feed nip 25 to the pair of nip rolls 14, 15 and the amount of deflection created by the rotating wheel 31. Furthermore, offsetting the rotating wheel's 31 axis of rotation or using cams can produce non-symmetrical tension profiles. As explained, the tension is often preferably higher in the crotch region 26 and lower in areas away from the crotch region 26. For example, the elongation range can be only 10% elongation in areas away from the crotch region 26 and in a range of around 250–300% elongation in the crotch region 26.

A wide variety of elastic materials may be used for the leg elastic members 58. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. A bonding device 11 is shown generally in FIGS. 7–9. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The leg elastic members 58 preferably have a width of about 0.05 inch to about 3 inches, more preferably about 0.15 inch to about 1.5 inches, most preferably about 0.25 inch to about 1.0 inch. The leg elastic members 58 preferably have elongation of 25–350%, more preferably about 30–260%, most preferably about 35–200%.

The substrate 13 is preferably the outer cover 40 and desirably includes a material that is substantially liquid impermeable, and can be elastic, stretchable or nonstretchable. The outer cover 40 can be a single layer of liquid impermeable material, but desirably includes a multilayered laminate structure in which at least one of the layers is liquid impermeable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and caregiver. A suitable liquid impermeable film for use as a liquid impermeable inner layer, or a single layer liquid i.:o impermeable outer cover 40, is a 0.02 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

As mentioned, the leg elastic members 58 can be bonded to the outer cover 40 and/or the bodyside liner 42. FIGS. 7–9 show the leg elastic members 58 being bonded to the outer cover 40 and the bodyside liner 42 at the same time. In this embodiment, the leg elastic members 58 are essentially sandwiched between the outer cover 40 and the bodyside liner 42.

The liquid permeable bodyside liner 42 is illustrated as overlying the outer cover 40 and absorbent assembly 44 (FIG. 3), and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly. The absorbent assembly 44 suitably has a density within the range of about 0.10 to about 0.35 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 grams per square meter, and including a through-air-bonded-carded web of a homogenous blend of 60 percent 3 denier bicomponent fiber including a polyester core/polyethylene sheath, commercially available from BASF Corporation, and 40 percent 6 denier polyester fiber, commercially available from Hoechst Celanese Corporation, in Portsmouth, Va., U.S.A.

As noted previously, the illustrated training pant 20 has front and back side panels 34 and 134 disposed on each side of the absorbent chassis 32 (FIGS. 1–3). These transversely opposed front side panels 34 and transversely opposed back side panels 134 can be permanently bonded to the composite structure 33 of the absorbent chassis 32 in the respective anterior and posterior sides 22 and 24, and are releasably attached to one another by a fastening system 80 (FIG. 1). More particularly, as shown best in FIG. 3, the front side panels 34 can be permanently bonded to and extend transversely beyond the linear side edges 47 of the composite structure 33 on the anterior side 22 along attachment lines 66, and the back side panels 134 can be permanently bonded to and extend transversely beyond the linear side edges of the composite structure on the posterior side 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover 40 or the bodyside liner 42.

In particular embodiments for improved fit and appearance, the side panels 34 and 134 desirably have an average length dimension measured parallel to the longitudinal axis 48 that is about 20 or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to the distal edge 68, as is best shown in FIG. 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material (See FIG. 1). Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between the distal edge 68 and a respective front or back center panel 35 or 135. In the illustrated embodiment in FIG. 3, the interior portions 78 are disposed between the distal edges 68 and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68 and a width of about 2 centimeters, are all elastomeric.

Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

The absorbent chassis 32 and the fastening system 80 together define a refastenable pant having a waist opening 50 and a pair of leg openings 52. When the fastening system is engaged, it can be appreciated that the refastenable pant includes a pair of elastomeric front side panels 34 extending from the waist opening to each leg opening, a pair of elastomeric back side panels 134 extending from the waist opening to each leg opening, a pair of refastenable seams 88 (FIG. 1) extending from the waist opening to each leg opening and positioned between the elastomeric front and back side panels, an elastomeric front waistband 54 disposed on the anterior side 22 and positioned between the pair of elastomeric front side panels, an elastomeric back waistband 56 disposed on the posterior side 24 and positioned between the pair of elastomeric back side panels, and at least a pair of the leg elastic members 58 which partially encircle each leg opening. Alternatively, instead of refastenable seams 88, the absorbent garment of the invention can have bonded side seams. More preferably, more than one leg elastic member 58 partially or fully encircles each leg opening 52. Each leg elastic member 58 extends from adjacent an elastomeric front side panel 34 on the anterior side 22 to adjacent an elastomeric back side panel 134 on the posterior side 24.

As described herein, the various components of the training pant 20 can be integrally assembled together employing various types of suitable attachment means, such as adhesive, sonic and thermal bonds or combinations thereof. The resulting product is an absorbent garment having optimized comfort, fit and containment about the leg openings 52.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent garment, comprising:

a waste containment section comprising an anterior side and a posterior side and defining first and second leg openings, a waist opening, and a crotch area between the anterior side and the posterior side; and a plurality of elastic members bonded to the absorbent garment about each of the leg openings, each of the elastic members extending continuously and substantially the same distance from the anterior side to the posterior side and none of the elastic members overlapping any other elastic member;

wherein tension in each of the bonded elastic members is asymmetrical about the leg openings with respect to the anterior and posterior sides.

2. The absorbent garment of claim 1 further comprising stretchable side panels connecting the anterior and posterior sides in a transverse direction.

3. The absorbent garment of claim 1 wherein the waste containment section further comprises an absorbent layer and a substantially liquid-impermeable outer cover layer.

4. The absorbent garment of claim 3, wherein the waste containment section further comprises a liquid-permeable body side liner.

5. The absorbent garment of claim 4, wherein the waste containment section further comprises a surge layer between the body side liner and the absorbent layer.

6. The absorbent garment of claim 3, wherein the outer cover comprises a plurality of layers, at least one of which is substantially liquid-impermeable.

7. The absorbent garment of claim 1, wherein the waste containment section further comprises elastic bands near the waist opening.

8. The absorbent garment of claim 1, comprising a diaper.

9. The absorbent garment of claim 1, comprising swim wear.

10. The absorbent garment of claim 1, comprising child training pants.

11. The absorbent garment of claim 1, comprising an incontinence product.

12. An absorbent garment, comprising:

a waste containment section comprising an anterior side and a posterior side and defining first and second leg openings, a waist opening, and a crotch area between the anterior side and the posterior side; and a plurality of elastic members bonded to the absorbent garment about each of the leg openings, each of the elastic members extending continuously and substantially the same distance from the anterior side to the posterior side and none of the elastic members overlapping any other elastic member;

wherein tension in each of the bonded elastic members is greater on the anterior side of the leg openings than on the posterior side of the leg openings.

13. The absorbent garment of claim 12, wherein tension in the bonded members is greater in the crotch area of the leg openings than on the posterior side of the leg openings.

14. An absorbent garment, comprising:

a waste containment section comprising an anterior side and a posterior side and defining first and second leg openings, a waist opening, and a crotch area between the anterior side and the posterior side; and a plurality of elastic members bonded to the absorbent garment about each of the leg openings, each of the elastic members extending continuously and substantially the same distance from the anterior side to the posterior side and none of the elastic members overlapping any other elastic member;

wherein a tension profile in at least one of the elastic members is asymmetrical about at least one of the leg openings with respect to the anterior and posterior sides and varies relative to a tension profile in an adjacent one of the elastic members.

15. The absorbent garment of claim 14 further comprising stretchable side panels connecting the anterior and posterior sides in a transverse direction.

16. The absorbent garment of claim 14 wherein the waste containment section further comprises an absorbent layer and a substantially liquid-impermeable outer cover layer.

17. The absorbent garment of claim 16, wherein the waste containment section further comprises a liquid-permeable body side liner.

18. The absorbent garment of claim 17, wherein the waste containment section further comprises a surge layer between the body side liner and the absorbent layer.

19. The absorbent garment of claim 16, wherein the outer cover comprises a plurality of layers, at least one of which is substantially liquid-impermeable.

20. The absorbent garment of claim 14, wherein the waste containment section further comprises elastic bands near the waist opening.

* * * * *